(12) United States Patent
Bonner, Jr. et al.

(10) Patent No.: US 7,053,073 B2
(45) Date of Patent: *May 30, 2006

(54) TREATMENT FOR REACTIVE ARTHRITIS OR BURSITIS

(75) Inventors: Ernest L. Bonner, Jr., Hillsborough, CA (US); Robert Hines, Fayetteville, NC (US)

(73) Assignee: Ficaar, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/896,612

(22) Filed: Jul. 20, 2004

(65) Prior Publication Data

US 2005/0059640 A1    Mar. 17, 2005

Related U.S. Application Data

(63) Continuation-in-part of application No. 10/271,117, filed on Oct. 15, 2002, now Pat. No. 6,765,000, which is a continuation-in-part of application No. 09/510,704, filed on Feb. 22, 2000, now Pat. No. 6,465,473, which is a continuation-in-part of application No. 09/270,962, filed on Mar. 17, 1999, now Pat. No. 6,087,382.

(51) Int. Cl.
 *A61K 31/65* (2006.01)
 *A61K 31/519* (2006.01)
 *A61K 31/415* (2006.01)

(52) U.S. Cl. ............... 514/152; 514/154; 514/262.1; 514/398

(58) Field of Classification Search ............. 514/152, 514/154, 262.1, 398
 See application file for complete search history.

(56) References Cited

U.S. PATENT DOCUMENTS

| | | | |
|---|---|---|---|
| 2,946,801 A | 7/1960 | Fields | |
| 3,148,212 A | 9/1964 | Boothe et al. | |
| 3,226,436 A | 12/1965 | Petisl et al. | |
| 4,177,796 A | 12/1979 | Franco-Vila | |
| 4,521,411 A | 6/1985 | Koloff | |
| 5,523,297 A | 6/1996 | Pruzanski et al. | |
| 5,952,367 A | 9/1999 | Pak | |
| 5,972,389 A | 10/1999 | Shell et al. | |
| 6,034,122 A | 3/2000 | Chayen | |
| 6,087,382 A | 7/2000 | Bonner, Jr. et al. | |
| 6,093,414 A | 7/2000 | Capelli | |
| 6,197,776 B1 | 3/2001 | Bonner, Jr. et al. | |
| 6,416,779 B1* | 7/2002 | D'Augustine et al. | 424/430 |
| 6,465,473 B1 | 10/2002 | Bonner, Jr. et al. | |
| 6,765,000 B1* | 7/2004 | Bonner et al. | 514/152 |
| 2002/0031558 A1* | 3/2002 | Yoo | 424/653 |
| 2002/0151519 A1 | 10/2002 | Shepard | |
| 2003/0055022 A1 | 3/2003 | Bonner, Jr. et al. | |
| 2005/0059640 A1 | 3/2005 | Bonner, Jr. et al. | |
| 2005/0137181 A1 | 6/2005 | Bonner, Jr. et al. | |
| 2005/0176690 A1 | 8/2005 | Bonner, Jr. et al. | |

OTHER PUBLICATIONS

Astrauskiene, D., "Efficacy of empirically prescribed amoxicillin and amoxicillin+ clavulanic acid in children's reactive arthritis: a randomized trial," Clin Exp Rheumatol. Jul.-Aug. 2003;21(4):515-21.

Ayoub et al., "Poststreptococcal Reactive Arthritis," Curr Opin Rheumatol. Jul. 2000;12(4):306-310.

Bardin, T., "Antimicrobial Therapy in Inflammatory Joint Disease," Rev Rhum Engl Ed. Nov. 1998;65(11):625-629.

Bardin et al., "Antibiotic Trials in Reactive Arthritis," Rev Rhum engl Ed. 1999 Jan. 30;66(1 suppl):63S-66S.

Bell et al., "Management of sexually acquired reactive arthritis in 19 North Thames GUM clinics," Int J STD AIDS, Mar. 2004;15(3):195-198.

Birdi et al., "Acute rheumatic feaver and poststreptococcal reactive arthritis: diagnostic and treatment practices of pediatric subspecialists in Canada,": J Rheumatol. Jul. 2001;28(7):1681-1688.

Brandt et al., "Effects of doxycycline on progression of osteoarthritis: results of a randomized, placebo-controlled, double-blind trial," Arthritis Rheum. Jul. 2005;52(7):2015-2025.

Burnette et al., "Purification and Characterization of a Rat Liver Enzyme that Hydrolyzes Valaciclovir, the $_1$-Valyl Ester Prodrug of Acyclovir," Chem. Abs. AN#1995;673023, J. Biol. Chem., 270(26), 15827-15831,(1995).

Ceroni et al., "Risks and complications of prolonged parenteral antibiotic treatment in children with acute osteoarticular infections," Acta Orthop Belg. Oct. 2003;69(5):400-404.

Fryden et al., "Early antibiotic treatment of reactive arthritis associated with enteric infections: clinical and serological study," BMJ, 1990 Dec. 8;301(6764): 1299-1302.

Hopkinson, N., "Sexually-acquired reactive arthritis," Hosp Med. Feb. 2001;62(2):83-85.

Kamphuisen et al., "Two years of penicillin prophylaxis is sufficient to prevent clinically evident carditis in poststreptocaccal reactive arthritis," J Intern Med. Nov. 2001;250(5):449-452.

Kloppenburg et al., "Antimicrobial therapy for rheumatoid arthritis," Baillieres Clin Rheumatol. Nov. 1995;9(4):759-769.

Kocak et al., "Poststretptococcal Reactive Arthritis: Clinical Course and Outcome in 15 Patients," Turk J Pediatri. Apr.-Jun. 2000;42(2):101-104.

Kvien et al., "Three month treatment of reactive arthritis with azithromycin: a EULAR double blind, placebo controlled study," Ann Rheum Dis. Sep. 2005;63(9):1113-1119.

Laasila et al., "Antibiotic treatment and long term prognosis of reactive arthritis," Ann Rheum Dis. Jul. 2003;62(7):655-658.

(Continued)

Primary Examiner—Raymond J. Henley, III
(74) Attorney, Agent, or Firm—Robins & Pasternak LLP

(57) ABSTRACT

A treatment for conditions in human beings associated with either or both reactive arthritis or bursitis comprising a combination of valacyclovir hydrochloride, minocycline hydrochloride, and metronidazole.

8 Claims, No Drawings

OTHER PUBLICATIONS

Lehman et al., "Clinical trials for post-streptococcal reactive arthritis," Curr Rheumamtol Rep. Oct. 2001;3(5):363-364.

Leirisalo-Repo, M., "Therapeutic aspects of spondyhloarthropathies - - a review," Scand J Rheumatol. 1998;27(5):323-328.

Loffler et al, "*Clostridium difficile*-associated reactive arthritis in two children," Joint Bone Spine. Jan. 2004;71(1):60-62.

Morfin Maciel et al., "Reactive polyarthritis and painful dermatographism caused by Helicobacter pylori," Rev Alerg Mex. May-Jun. 2002;49(3):99-102. Article in Spanish; abstract only is provided in English.

Neumayr et al., "Chronic reactive arthritis associated with Calmette-Guerin bacillus," Dtsch Med Wochenschr. Sep. 13, 2002;127(37):1886-1888. Article in German; abstract only is provided in English.

Palazzi et al., "Reactive arthritis: advances in diagnosis and treatment," Reumatismo. Apr.-Jun. 2002;54(2):105-112. Article in Italian; abstract only is provided in English.

Palazzi et al., "Management of reactive arthritis," Expert Opin Pharmacother. Jan. 2004;5(1):61-70.

Pappas et al., "Unusual causes of reactive arthritis: Leptospira and Coxiella burnetii," Clin Rheumatol. Oct. 2003;22(4-5):343-346.

Pott et al. letter, "Long-term antibiotic treatment in reactive arthritis," Lancet. Jan.30, 1988;1(8579):245-246.

Shulman et al., "Poststreptococcal reactive arthritis." Curr Opin Rheumatol. Sep.2000;14(5);562-565.

Sieper et al., "Report on the Fourth International Workshop on Reactive Arthritis," Apr. 2000; Arhritis Rheum. Apr. 2000;43(4):720-734.

Sieper, J., "Reactive arthritis: practical procedure in diagnosis and problematic aspects of antibiotic therapy," Z Rheumatol. Apr. 2003;62(2):110-111. Article in German; abstract only is provided in English.

Sieper et al., "No benefit of long-term ciprofloxacin treatment in patients with reactive arthritis and undifferentiated oligoarthritis: a three-month, multicenter, double-blind, randomized, placebo-controlled study," Arthritis Rheum. Jul. 1999;42(7):11386-11396.

Sieper et al., "Expert Witness Reports in Rheumatology," British Society for Rheumatology, 1998;37:715-720.

Smieja et al., "Randomised, blinded, placebo controlled trial of doxycycline for chronic seronegative arthritis," Ann Rheum Dis. Dec. 2001;60(12):1088-1094.

Svenungsson, B., "Reactive arthritis," Int J STD AIDS. May-Jun. 1995;6(3):156-160.

Toivanen et al., "Reactive Arthritis," Curr Opin Rheumatol. Jul. 1997;9(4):321-327.

Toivanen et al., "Effect of antimicrobial treatment on chronic reactive arthritis," Clin Exp Rheumatol. May-Jun. 1993;11(3):301-307.

Toivanen et al., "Reactive arthritis," Best Practice & Research Clinical Rheumatology, Oct. 2004;18(5):689-703.

Toivanen, A., "Bacteria-Triggered reactive arthritis: implications for antibacterial treatment," Drugs. 2001;61(3):343-351.

Zhang et al., "Experimental Yersinia-triggered reactive arthritis: effect of a 3-week course of ciprofloxacin," Br J Rheumatol. May 1997;36(5):541-546.

* cited by examiner

TREATMENT FOR REACTIVE ARTHRITIS OR BURSITIS

CROSS-REFERENCES TO RELATED APPLICATIONS

This application is a continuation-in-part of U.S. patent application Ser. No. 10/271,117 filed Oct. 15, 2002, now U.S. pat. No. 6,765,000, which is a continuation-in-part of U.S. patent application Ser. No. 09/510,704, filed Feb. 22, 2000, now U.S. Pat. No. 6,465,473, which is a continuation-in-part of Application Ser. No. 09/270,962, filed Mar. 17, 1999, now U.S. Pat. No. 6,087,382.

BACKGROUND OF THE INVENTION

This invention relates to an improved pharmaceutical formulation for treatment of symptoms in humans associated with reactive arthritis or idiopathic bursitis.

Reactive arthritis commonly occurs in young men and women, but can occur at any age. Sufferers experience joint pain, stiffness, redness or swelling. Common symptoms may include fatigue, malaise, fever, and weight loss. The joints of the lower extremities, including the knee, ankle, and joints of the foot, are the most common sites of involvement, but symptoms can also occur in the wrists, fingers, elbows, shoulders, neck, and lower back. Other symptoms may include urethritis and prostatitis in males, and cervicitis or salpingitis in females. Ocular disease is common ranging from transient, asymptomatic conjunctivitis to aggressive anterior uveitis that occasionally results in blindness. Mucocutaneous lesions and nail changes are frequent. On less frequent or rare occasions manifestations of reactive arthritis include cardiac conduction defects, aortic insufficiency, central or peripheral nervous system lesions, and pleuropulmonary infiltrates.

Treatment of patients suffering from reactive arthritis with nonsteroidal anti inflammatory drugs ("NSAID") provides some benefit, although symptoms of reactive arthritis are rarely completely alleviated and some patients fail to respond at all. The preferred initial treatment of choice for acute reactive arthritis is indomethacin in divided doses of 75 to 150 milligrams per day. The NSATD of last resort is phenylbutazone, in doses of 100 milligrams twice or three times per day, because of its potentially serious side effects. Patients with debilitating symptoms refractory to NSAJD therapy may be treated with cytotoxic agents such as azathioprine or methotrexate, or with sulfasalazine. Tendinitis, other lesions, and uveitis may benefit from corticosteroids. Minocycline hydrochloride, a semisynthetic derivative of tetracycline, is indicated for infections caused by at least Shigella microorganisms, Streptococcus pyogenes, and Neisserie gonorrhoeae. It is therefore an accepted treatment in incidents of reactive arthritis triggered by these biological entities.

Long-term follow-up studies have suggested that some joint symptoms persist in many, if not most, patients with reactive arthritis. Recurrences of the more acute symptoms are common and as many as twenty-five percent of patients either become unable to work or are forced to change occupations because of persistent joint problems.

Bursitis is inflammation of a bursa, a thin-walled sac lined with synovial tissue. The function of the bursa is to facilitate movement of tendons and muscles over bony prominences. Bursitis may be caused by excessive frictional forces, trauma, systemic disease such as rheumatoid arthritis or gout, or infection. The most common form of bursitis is subacromial. Trochanteric bursitis causes patients to experience pain over the lateral aspect of the hip and upper thigh, and tenderness over the posterior aspect of the greater trochanter. Retrocalcaneal bursitis involves the bursa located between the calcaneus and the posterior surface of the Achilles tendon. Pain is experienced at the back of the heel, and swelling appears on either or both of the medial and lateral sides of the tendon. Retrocalcaneal bursitis occurs in association with spondyloarthritities, rheumatoid arthritis, gout, and trauma.

Treatment of bursitis generally consists of prevention of the aggravating condition, rest of the involved part, an NSAID, and local steroid injection. In the long term, bursitis can result in loss of use of a joint and chronic pain syndrome.

The long term effects of reactive arthritis and bursitis range from chronic pain to crippling disability. It is also thought that many instances of osteoarthritis and psoriatic arthritis are in actuality reactive arthritis. Unfortunately, current procedures for management treat the symptoms of these diseases rather than their underlying pathogens.

SUMMARY OF THE INVENTION

The inventors have discovered that significant benefits can be obtained by treating humans affected with conditions associated with reactive arthritis or bursitis using combinations of acyclovir, minocycline hydrochloride, and metronidazole or, alternatively, valacyclovir hydrochloride, minocycline hydrochloride, and metronidazole.

Acyclovir is an anti-viral drug. The chemical name of acyclovir is 2-amino-1,9-dihydro-9-[(2-hydroxyethoxy)methyl]-6H-purin-6-one. Acyclovir is commercially available under the brand name ZOVIRAX® in capsules, tablets, or suspension. Acyclovir has demonstrated anti-viral activity against herpes simplex virus types I and II, varicella-zoster virus, Epstein-Barr virus and cytomegalovirus, both in vitro and in vivo.

Valacyclovir hydrochloride (sold under the brand name Valtrex® is the hydrochloride salt of L-valyl ester of acyclovir. The chemical name of valacyclovir hydrochloride is L-valine 2-[(2-amino-1,6-dihydro-6-oxo-9H-purin-9-yl) methoxy]ethyl ester, monohydrochloride. Valacyclovir hydrochloride is rapidly and nearly completely converted to acyclovir in the body.

Minocycline hydrochloride is a bacteriostatic antibiotic which exerts its antimicrobial effect by inhibition of bacterial protein synthesis. It has been shown to be effective against gram-negative bacteria, some gram-positive bacteria and other microorganisms.

Metronidazole is an oral synthetic antiprotozoal and antibacterial agent. Heretofore it has been indicated for treatment of symptomatic trichomoniasis, intestinal amebiasis, and a wide range of intra-abdominal, skin, and gynecological, bone and joint, and lower respiratory tract and central nervous system infections, bacterial septicemia and endocarditis.

One embodiment of a formulation for treatment of the symptoms in human beings of reactive arthritis or idiopathic bursitis, or both, comprises the combination of acyclovir, minocycline hydrochloride, and metronidazole. An alternative formulation comprises the substitution of valacyclovir hydrochloride in place of acyclovir. The pharmaceutical dosages of the compounds of the combination may be administered in capsules, tablets, in suspension form, or by injection.

The invention provides a pharmaceutical combination that puts the diseases of reactive arthritis and bursitis into remission. Treatment with the combination may effect a cure of reactive arthritis and bursitis, but definitive testing has not been performed to confirm that fact.

It is therefore a primary object of the invention to provide a combination for treating conditions in human beings associated with either or both reactive arthritis or idiopathic bursitis.

Another object of the invention is to provide a treatment for conditions in human beings associated with either or both reactive arthritis or idiopathic bursitis that puts the disease being treated into full remission.

A further object of the invention is to provide a treatment for any constellation of symptoms amenable to treatment using the above combination, including for example, cases of reactive arthritis which have been misdiagnosed as osteoarthritis or psoriatic arthritis.

A still further object of the invention is to provide a combination comprising a pharmaceutical carrier for treating conditions in human beings associated with either or both reactive arthritis or idiopathic bursitis.

DETAILED DESCRIPTION OF THE INVENTION

Application Ser. No. 09/270,962, now U.S. Pat. No. 6,087,382, describes a method of treatment involving administration of a combination of L-lysine, minocycline hydrochloride, and metronidazole. An alternate method includes administration of InH for those individuals who have tested positively for mycobacterial exposure, along with the underlying combination of L-lysine, minocycline hydrochloride, and metronidazole. Another method described in application Ser. No. 09/510,704, now U.S. Pat. No. 6,465,473, includes administration of valacyclovir hydrochloride with the underlying combination of L-lysine, minocycline hydrochloride, and metronidazole. A third method of treatment, described in applicants' application Ser. No. 09/613,876, now U.S. Pat. No. 6,197,776, includes administration of acyclovir with the underlying combination of L-lysine, minocycline hydrochloride, and metronidazole. An embodiment of the treatment, described in applicants' U.S. patent application Ser. No. 10/271,117, comprises a pharmaceutical combination including acyclovir, minocycline hydrochloride, and metronidazole. Alternatively, the treatment may include valacyclovir hydrochloride, minocycline hydrochloride, and metronidazole. Either of these embodiments may be supplemented with administration of pyridoxine hydrochloride, glucosamine, manganese, vitamin C, and desalinated seawater, such as Essence of Life.

Administration will generally be accomplished orally via capsules, tablets, or in suspension form, but delivery could be accomplished by injection, or any other method commonly used for administration of internal medicines.

Like L-lysine, acyclovir inhibits herpes simplex viruses, but by a different mechanism. While L-lysine tends to stop the virus from replicating by inhibiting the initiation of the replication process, acyclovir inhibits effective replication of actively replicating viral particles by stopping replication of herpes viral DNA. This is accomplished by either competitive inhibition or inactivation of viral DNA polymerase or incorporation an termination of the growing viral DNA chain. It is believed that acyclovir results in a substantial benefit due to its inhibition of virus replication. In double-blind testing, it has been found that the administration of the combination of acyclovir, minocycline hydrochloride, and metronidazole is an effective treatment for reactive arthritis or bursitis. Acyclovir has never been used in the prior art for treatment of arthritis or bursitis. It does not appear to be effective alone for the treatment of these diseases. The preferred dose of acyclovir is 400 mg twice daily. The daily dose of acyclovir may vary from 200 mg to 4 grams.

The preferred dose of valacyclovir hydrochloride is 500 mg twice daily. The total daily dose of valacyclovir may vary from 125 mg to 4 grams.

The preferred dose of minocycline hydrochloride is an initial dosage of 200 mg followed by doses of 100 mg twice per day. Daily doses of minocycline hydrochloride following the initial administration of 200 mg may vary from 50 mg to 200 mg. Based upon their similar properties, it is expected that other members of the tetracycline family such as doxycycline can be effectively substituted, in the combination, for minocycline hydrochrloride.

The preferred dose of metronidazole is 250–500 mg twice per day. The total dose per day of metronidazole may vary from 100 mg to 1,000 mg.

It is known that the combination of minocycline hydrochloride, InH, and metronidazole inhibits the multiplication of susceptible organisms, including *shigella, salmonella, chlamydia, streptococci*, and *mycobacteria*. Applicants have also determined that the combination of L-lysine, minocycline hydrochloride, and metronidazole provides a medically effective treatment for reactive arthritis and bursitis. See U.S. Pat. No. 6,087,382. It has also been shown that the combination of acyclovir, L-lysine, iminocycline hydrochloride, and metronidazole provides an effective treatment for these conditions. See U.S. Pat. No. 6,197,776. Individuals with severe symptoms, including joint swelling and joint contractures, who were not thought to be candidates for treatment using the combination of L-lysine, minocycline hydrochloride, and metronidazole only, have also experienced substantial beneficial effects in response to treatment with that combination and valacyclovir hydrochloride.

The preferred embodiment of the present invention comprises the combination of valacyclovir with minocycline hydrochloride and metronidazole. This combination provides a medically effective treatment for reactive arthritis and bursitis. The total combination of medicines in each of these embodiments presents a broad spectrum approach that it is believed effectively addresses the underlying pathogenesis for reactive arthritis and what has previously been referred to as idiopathic bursitis, and further is a beneficial treatment for reactive arthritis in particular cases wherein the symptom complex has been misdiagnosed as osteoarthritis or psoriatic arthritis, or in any other similar cases of misdiagnosis.

EXAMPLE

The following example serves to illustrate the invention, but is not meant to restrict its effective scope.

A 77 year old female presented with complaints of neck, upper back, lower bak, bilateral shoulder, bilateral wrist, digits of hands, bilateral hip, and bilateral ankle pains of years duration. The patient complained of associated stiffness in those same joints. Her physical examination was remarkable for tenderness at her neck, right shoulder, elbow bilaterally, wrist bilaterally, the metacarpal phalangeal and the proximal interphalangeal joints of her right hand; hip bilaterally, knee bilaterally, and the Achilles insertion area bilaterally. The sed rate and rheumatoid factors were normal. This patient was diagnosed with reactive arthritis and was started on a single pill item consisting of 125 mg of metronidazole, 250 mg of valacyclovir hydrochloride, and 50 mg of minocycline hydrochloride twice daily. After 69 days of such treatment, the patient noted pain in the palm of her left hand only. She further denied any stiffness. physical examination on the 69$^{th}$ day did not reveal any tenderness. Thus, treatment effected resolution of pain, stiffness, and tenderness in this patient.

There have been thus described certain preferred embodiments of a pharmaceutical formulation for treatment of conditions in human beings associated with either or both reactive arthritis or idiopathic bursitis. While preferred embodiments have been described and disclosed, it will be recognized by those with skill in the art that modifications are within the true scope and spirit of the invention. The appended claims are intended to cover all such modifications.

We claim:

1. A pharmaceutical formulation for use in treating reactive arthritis or bursitis in a mammal, including a human, comprising:

an effective amount of the combination of a first dosage unit comprising valacyclovir hydrochloride, a second dosage unit comprising a member of the tetracycline family, and a third dosage unit comprising metronidazole.

2. A pharmaceutical formulation of claim 1 wherein:

said member of the tetracycline family is minocycline hydrochloride.

3. A pharmaceutical formulation of claim 2 in association with one or more pharmaceutically acceptable carriers.

4. A formulation of claim 2 in a form suitable for oral administration.

5. A formulation of claim 3 wherein:

said first dosage unit comprises from 125 mg to 4 gm of valacyclovir hydrochloride, said second dosage unit comprises from 50–200 mg of minocycline hydrochloride, and said third dosage unit comprises from 100–1,000 mg metronidazole.

6. A pharmaceutical formulation of claim 5 wherein:

said first dosage unit comprises 500 mg of valacyclovir hydrochloride, said second dosage unit comprises 100 mg of minocycline hydrochloride, and said third dosage unit comprises 250 mg of metronidazole.

7. A pharmaceutical formulation for use in treating reactive arthritis or bursitis in a mammal, including a human, comprising:

in association with one or more pharmaceutically acceptable carriers, a combination of a first dosage unit comprising from 200 mg to 4 gm of acyclovir, a second dosage unit comprising from 50–200 mg of minocycline hydrochloride, and a third dosage unit comprising from 100–1,000 mg of metronidazole.

8. A pharmaceutical formulation of claim 7 wherein:

said first dosage unit comprises 400 mg of acyclovir, said second dosage unit comprises 100 mg of minocycline hydrochloride, and said third dosage unit comprises 250 mg of metronidazole.

* * * * *